(12) United States Patent
Tobita et al.

(10) Patent No.: US 10,524,747 B2
(45) Date of Patent: Jan. 7, 2020

(54) HOLDING MECHANISM FOR OPERATION DEVICE AND X-RAY IMAGING UNIT

(71) Applicant: OMRON CORPORATION, Kyoto-shi, Kyoto (JP)

(72) Inventors: Kokichi Tobita, Unnan (JP); Masataka Kimura, Ichinomiya (JP); Koichi Furusawa, Okayama (JP)

(73) Assignee: OMRON CORPORATION, Kyoto-shi (JP)

(*) Notice: Subject to any disclaimer, the term of this patent is extended or adjusted under 35 U.S.C. 154(b) by 132 days.

(21) Appl. No.: 15/573,611

(22) PCT Filed: Jul. 25, 2016

(86) PCT No.: PCT/JP2016/071772
§ 371 (c)(1),
(2) Date: Nov. 13, 2017

(87) PCT Pub. No.: WO2017/022549
PCT Pub. Date: Feb. 9, 2017

(65) Prior Publication Data
US 2018/0085074 A1    Mar. 29, 2018

(30) Foreign Application Priority Data
Aug. 6, 2015 (JP) ................. 2015-156474

(51) Int. Cl.
*A61B 6/00* (2006.01)

(52) U.S. Cl.
CPC .......... *A61B 6/4411* (2013.01); *A61B 6/4405* (2013.01); *A61B 6/54* (2013.01);
(Continued)

(58) Field of Classification Search
None
See application file for complete search history.

(56) References Cited

U.S. PATENT DOCUMENTS

| | | | |
|---|---|---|---|
| 5,206,894 A | 4/1993 | Makrinos et al. | |
| 5,246,183 A | 9/1993 | Leyden | |
| | (Continued) | | |

FOREIGN PATENT DOCUMENTS

| | | | |
|---|---|---|---|
| JP | 2002-186059 A | 6/2002 | |
| JP | 2003-210445 A | 7/2003 | |
| | (Continued) | | |

OTHER PUBLICATIONS

English translation of Written Opinion of PCT/JP2016/071772 dated Feb. 15, 2018 from the International Searching Authority.
(Continued)

*Primary Examiner* — Hoon K Song
(74) *Attorney, Agent, or Firm* — Metrolex IP Law Group, PLLC (57) ABSTRACT

A holder (100) included in an X-ray imaging device holds an operation device for wirelessly operating the X-ray imaging device in a removable manner. The holder (100) sets the operation device unremovable when the X-ray imaging device is not in operation, and sets the operation device removable when the X-ray imaging device is in operation. This easily prevents the X-ray imaging device from being brought away.

6 Claims, 6 Drawing Sheets

(52) U.S. Cl.
CPC ................ *A61B 6/548* (2013.01); *A61B 6/56* (2013.01); *A61B 6/40* (2013.01)

(56) References Cited

U.S. PATENT DOCUMENTS

| | | |
|---|---|---|
| 2005/0231485 A1 | 10/2005 | Jones et al. |
| 2006/0114431 A1 | 6/2006 | Ushiro |
| 2013/0170619 A1* | 7/2013 | Kamitake ................ A61B 6/00 378/62 |
| 2014/0053185 A1* | 2/2014 | Bleacher .......... H04N 21/41422 725/26 |
| 2014/0354964 A1 | 12/2014 | Ogawa |

FOREIGN PATENT DOCUMENTS

| | | |
|---|---|---|
| JP | 2006-154260 A | 6/2006 |
| KR | 20-0196178 Y1 | 9/2000 |
| WO | 2011/132363 A1 | 10/2011 |
| WO | 2015/112336 A1 | 7/2015 |

OTHER PUBLICATIONS

The Japanese Office Action dated Feb. 7, 2017 in a counterpart Japanese patent application.
The (translated) International Search Report of PCT/JP2016/071772 dated Oct. 18, 2016.
The Australian Office Action dated Mar. 29, 2019 in a counterpart Australian patent application.
The Korean Office Action dated Apr. 15, 2019 in a counterpart Korean patent application.

\* cited by examiner

HOLDING MECHANISM FOR OPERATION DEVICE AND X-RAY IMAGING UNIT

FIELD

The present invention relates to a holding mechanism for an operation device, and an X-ray imaging unit.

BACKGROUND

An X-ray imaging device known in the art irradiates a patient with X-rays and detects the X-rays transmitted through the patient to generate images. The X-ray imaging device is usually operated using a wired operation device.

An X-ray imaging device may be operated with a wireless operation device. For example, an X-ray imaging device described in Patent Literature 1 is operable with a remote controller using radio waves or infrared rays.

CITATION LIST

Patent Literature

Patent Literature 1: U.S. Pat. No. 5,206,894

SUMMARY

Technical Problem

Previously, the X-ray imaging device is usually used in an imaging room. The wireless remote controller described in Patent Literature 1 may thus simply be placed in a drawer that is locked by an imaging engineer. Nowadays, the X-ray imaging device is often carried around in a hospital for imaging. Measures are to be taken to prevent the operation device from being brought away by a third party. This issue is not limited to the X-ray imaging device and is common to any device with a wireless remote controller.

In response to the above issue, one or more aspects of the present invention are directed to a holding mechanism for an operation device that is prevented easily from being brought away, and an X-ray imaging unit.

Solution to Problem

In response to the above issue, one or more aspects of the present invention are directed to a holding mechanism included in a main unit for holding an operation device in a removable manner. The operation device is used to operate the main unit wirelessly. The holding mechanism includes a bringing-away preventive unit that sets the operation device unremovable when the main unit is not in operation, and sets the operation device removable when the main unit is in operation.

Advantageous Effects

The holding mechanism according to the above aspects of the present invention easily prevents the operation device from being brought away.

DETAILED DESCRIPTION

Figure 1:
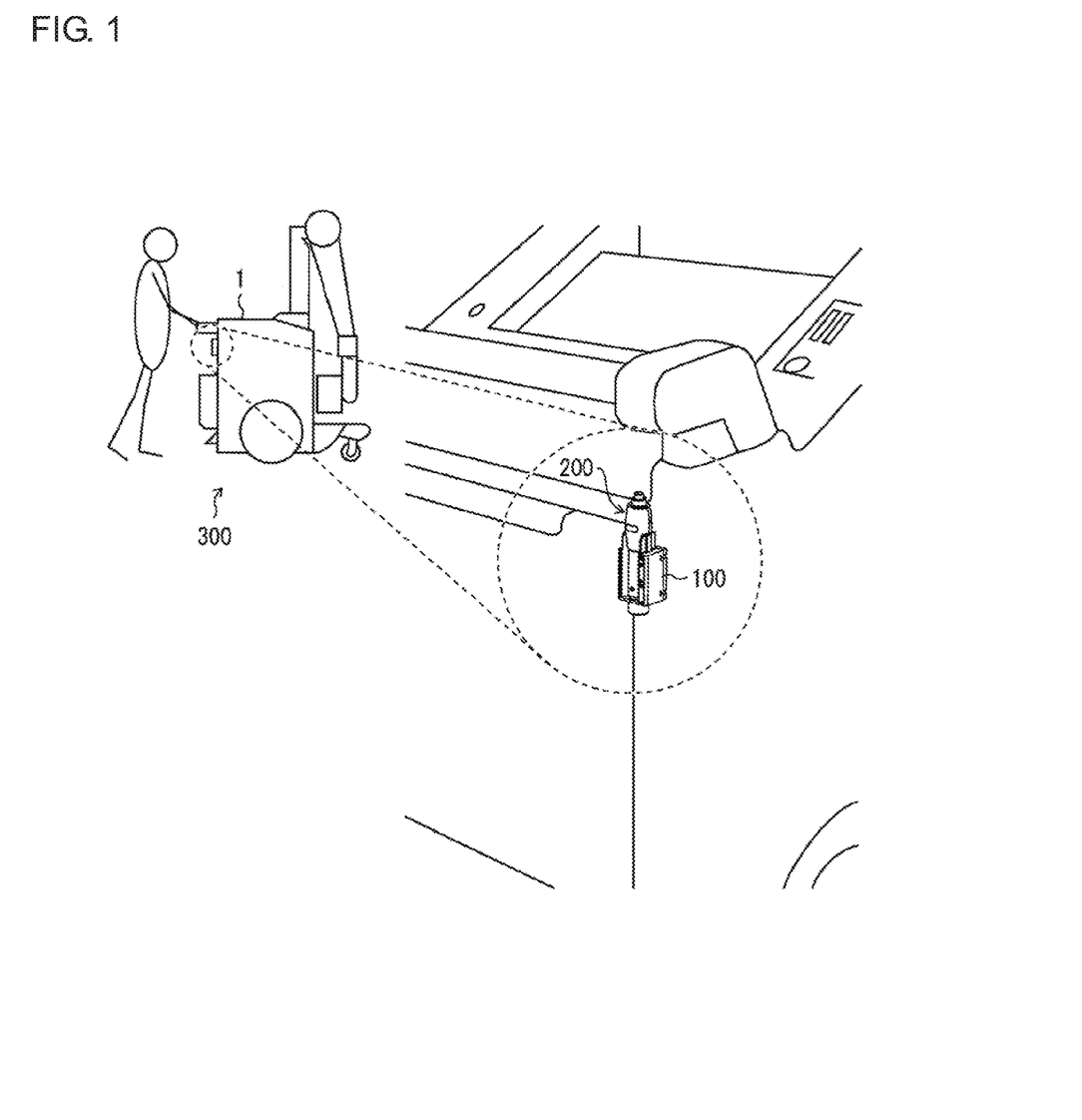
FIG. 1 is an external view of an X-ray imaging unit according to one embodiment.
Figure 2:
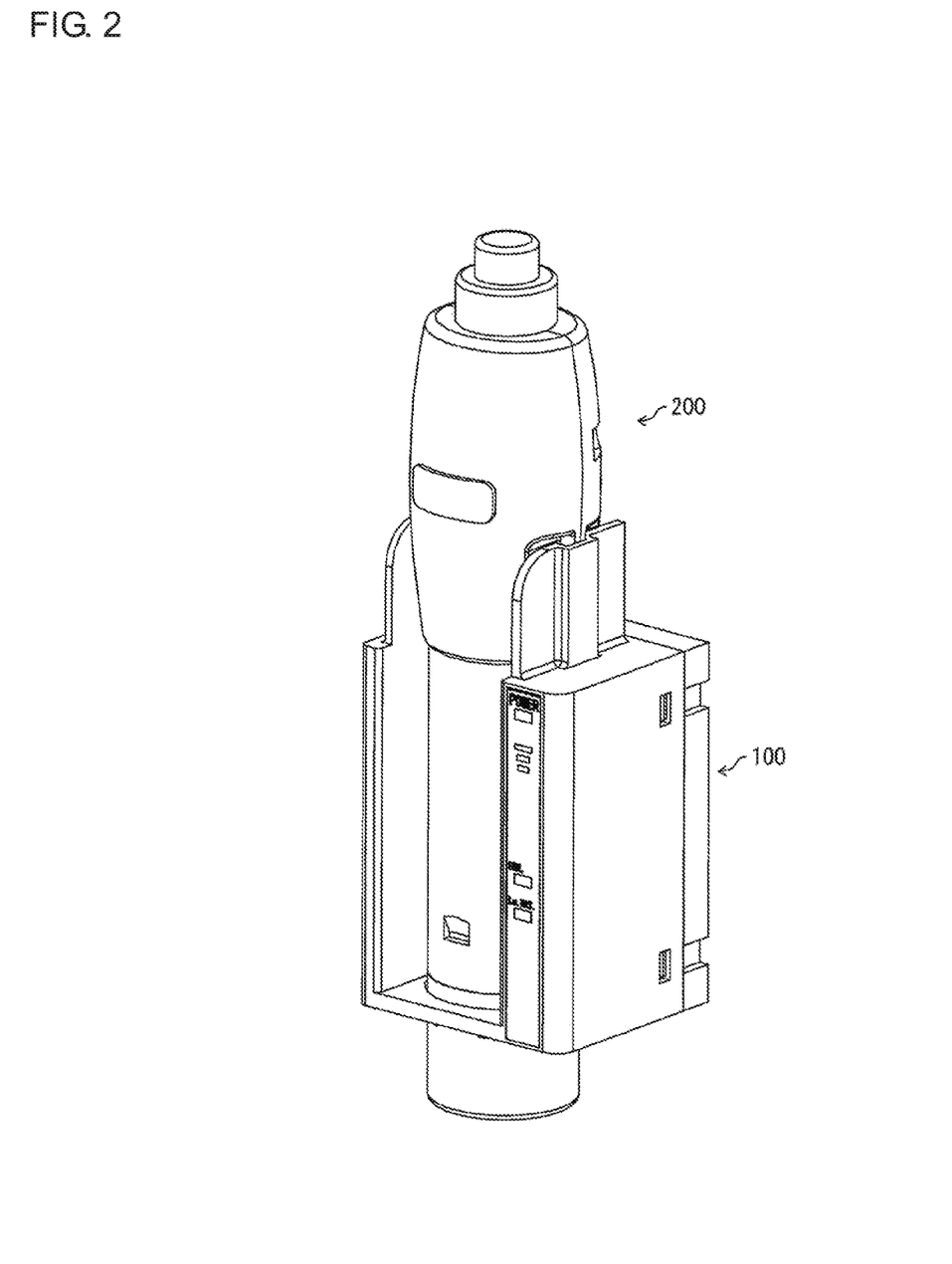
FIG. 2 is a perspective view of an operation device with a holder for operating a main unit according to the embodiment.

Embodiments of the present invention will now be described in with reference to the drawings. FIG. 1 is an external view of an X-ray imaging unit according to one embodiment. FIG. 2 is a perspective view of an operation device with a holder for operating a main unit according to the present embodiment.

As shown in FIGS. 1 and 2, an X-ray imaging unit 300 irradiates a patient with X-rays and detects the X-rays transmitted through the patient to generate X-ray images. The X-ray imaging unit 300 includes an X-ray imaging device (main unit) 1, a holder (holding mechanism) 100, and an operation device 200. The X-ray imaging device 1 includes the holder 100 that, holds the operation device 200 in a removable manner.

FIGS. 3A to 3B and FIGS. 4A to 4D are diagrams showing the operation device in the present embodiment. The operation device 200 is a remote controller for wirelessly operating the X-ray imaging device 1.

Figure 3A:
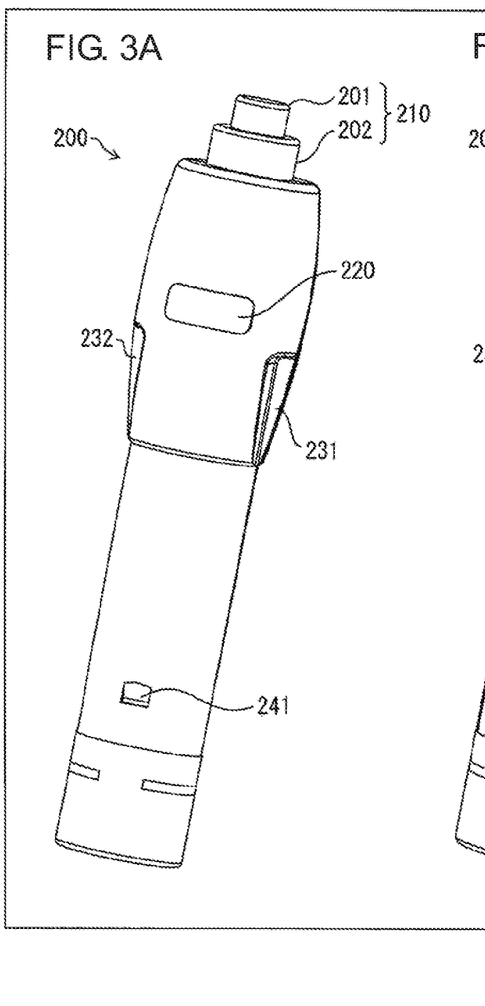
FIGS. 3A and 3B are diagrams showing the operation device according to the embodiment.
Figure 3B:
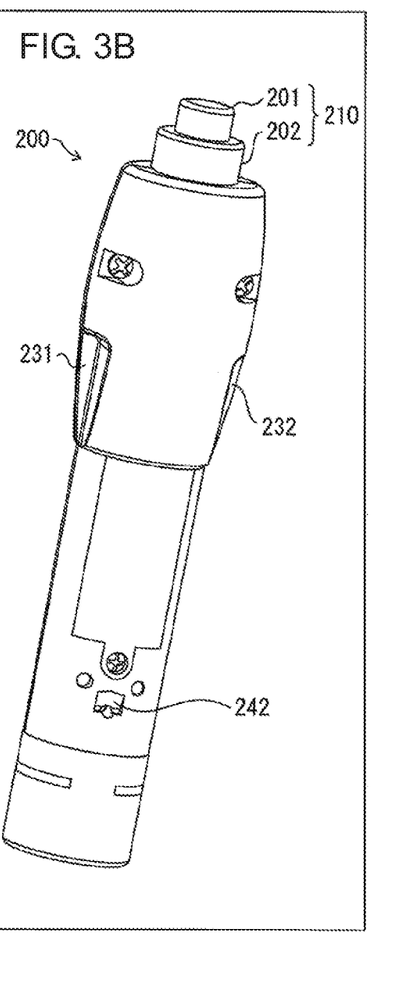

As shown in FIGS. 3A and 3B, the operation device 200 is substantially cylindrical. The operation device 200 includes a main switch 210 on its upper surface and an optional switch 220 in an upper portion of its peripheral surface to allow the user gripping the peripheral surface of the operation device 200 to operate the main switch 210 with a thumb and the optional switch 220 with a forefinger. The operation device 200 will be described, referring to its side with the optional switch 220 as the front surface, and the opposite side as the back surface.

The operation device 200 includes the main switch 210 to be pressed to output an instruction for X-ray imaging to the X-ray imaging device 1, and the optional switch 220 to be pressed to output, to the X-ray imaging device 1, an instruction for turning on or off a lighting instrument included in the X-ray imaging device 1.

More specifically, the main switch 210, which operates in two stages, includes first and second switch members 201 and 202 set at different, home positions when not pressed by the user. The first switch member 201 has a longer stroke distance from its home position than the second switch member 202.

Figure 4A:
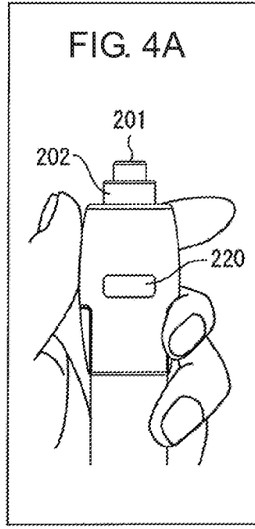
FIGS. 4A to 4D are diagrams describing the operating procedure of the operation device according to the embodiment.
Figures 4B, 4C:
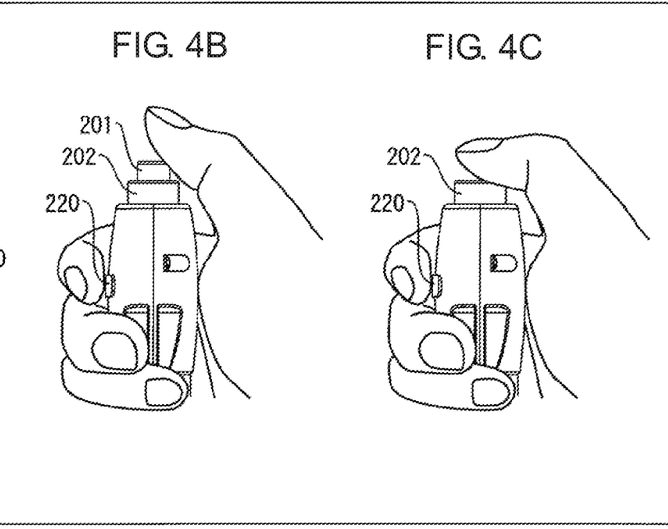
Figure 4D:
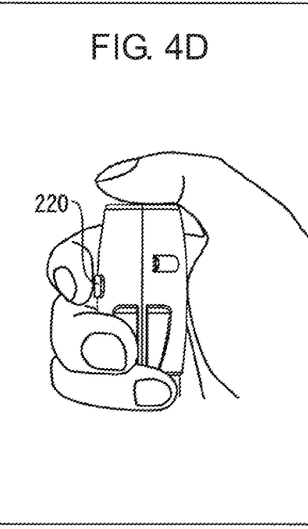

When the user presses the first switch member 201 to the home position of the second switch member 202, the operation device 200 outputs an instruction for charging an X-ray imaging circuit (through the holder 100) to the X-ray imaging device 1 (refer to FIGS. 4A to 4C). When the first switch member 201 remains in the pressed state for a predetermined time, the X-ray imaging circuit is fully charged and becomes ready for imaging. When both the first switch member 201 and the second switch member 202 are pressed to the full-stroke position, the operation device 200 outputs an instruction for X-ray imaging (through the holder 100) to the X-ray imaging device 1 (refer to FIG. 4D).

The operation device 200 can be housed in and locked by the holder 100 arranged in the X-ray imaging device 1. The operation device 200 has engagement holes 241 and 242, and grooves 231 and 232 on its peripheral surface. More specifically, the operation device 200 includes a first engagement hole 241 at a lower position than the optional switch 220 on its front surface, and a second engagement hole 242 on its back surface at a position corresponding to the first engagement hole 241. The grooves 231 and 232 are formed on both joints between the front surface and the back surface. Each of the grooves 231 and 232 is located in around the middle of the side surface.

Figure 5:
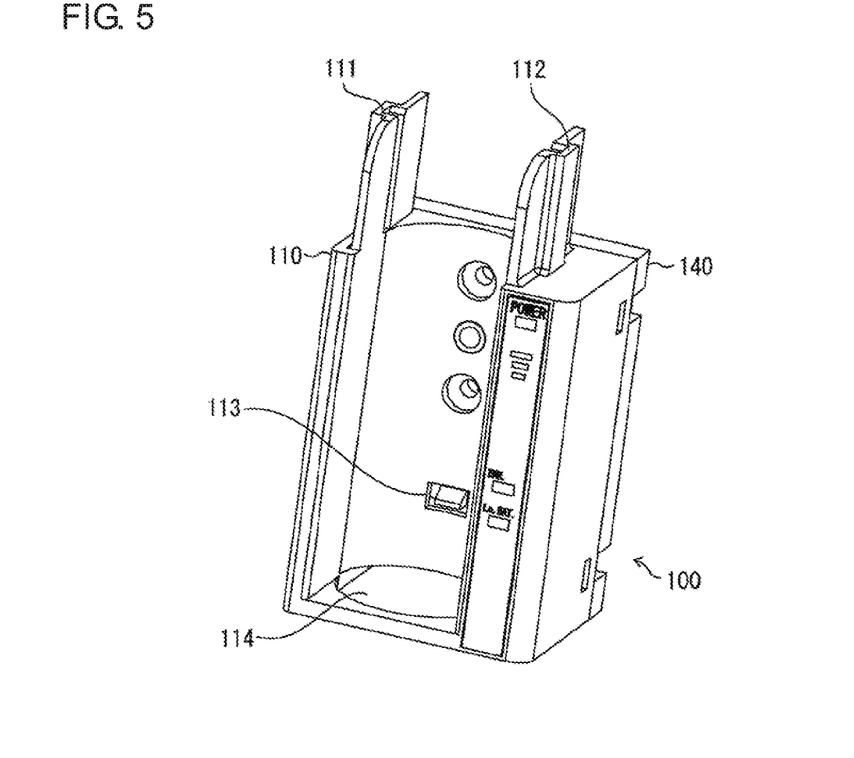
FIG. 5 is a diagram showing the holder according to the embodiment.

FIG. 5 is a diagram showing the holder in the present embodiment. As shown in FIG. 5, the holder 100 includes a box-shaped holder body 110 with an open front and an open top, a lock mechanism (bringing-away preventive unit) 130 (refer to FIGS. 6 and 7A to 7D), and a cover 140, which is attached to the back surface of the holder body (contact member) 110. The holder body 110 has an opening 114 in its lower surface, through which the operation device 200 can be inserted, and guides 111 and 112 on its two side surfaces for holding the operation device 200. More specifically, when the bottom of the operation device 200 is inserted into the opening 114, the grooves 231 and 232 in the operation device 200 are slidably fitted in the guides 111 and 112 to hold the operation device 200 in place in the holder body 110.

The operation device 200 is housed with its front surface (including the optional switch 220 and the first engagement hole 241) exposed in front, and its back surface located at the back.

The holder 100 further includes a lock mechanism 130 on its back surface for locking the operation device 200. The lock mechanism 130 locks the operation device 200 when the X-ray imaging device 1 is powered off (or not in operation), and unlocks the operation device 200 when the X-ray imaging device 1 is powered on (or in operation).

Figure 6:
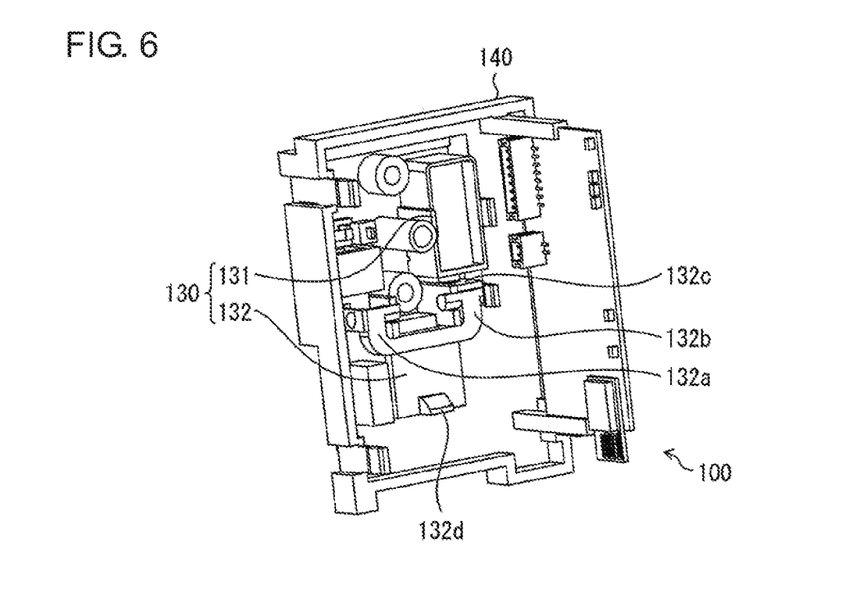
FIG. 6 is a diagram showing the internal structure of the holder according to the embodiment.

FIG. 6 is a diagram showing the internal structure of the holder. FIGS. 7A to 7D are cross-sectional views of the operation device that is held in the holder. As shown in FIGS. 6 and 7A to 7D, the holder 100 includes, on its back surface, the lock mechanism 130 including a solenoid (drive) 131, a movable plate (movable member) 132, and a coil spring (elastic member) 133. The movable plate 132 has U-shaped ends 132a and 132b, which are supported pivotally. The end 132b has a bend 132c, which is connected to the solenoid 131 with a plunger.

The movable plate 132 further has a hook 132d on its end opposite to the pivoted. ends 132a and 132b. The hook 132d protrudes toward the front of the holder body 110. The hook 132d has a sloping surface in the direction in which the operation device 200 is inserted.

The holder body 110 also has a hole 113 that allows the hook 132d to protrude as the movable plate 132 moves. The hole 113 faces the second engagement hole 242 in the operation device 200 when the operation device is held in the holder. The coil spring 133 is arranged between the cover 140 and the movable plate 132. The coil spring 133 urges the movable plate 132 toward the front of the holder body 110.

Figures 7A, 7B:
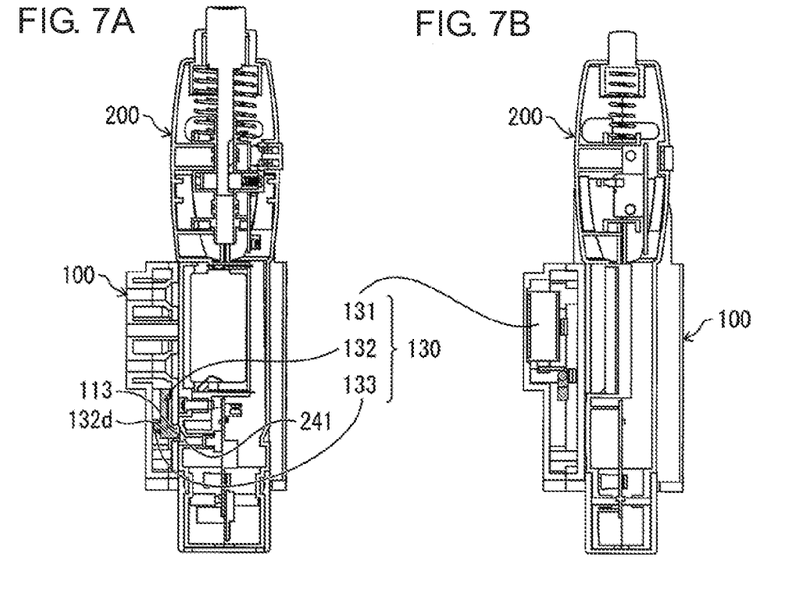
FIGS. 7A to 7D are cross-sectional views of the operation device that is held in the holder.
Figures 7C, 7D:
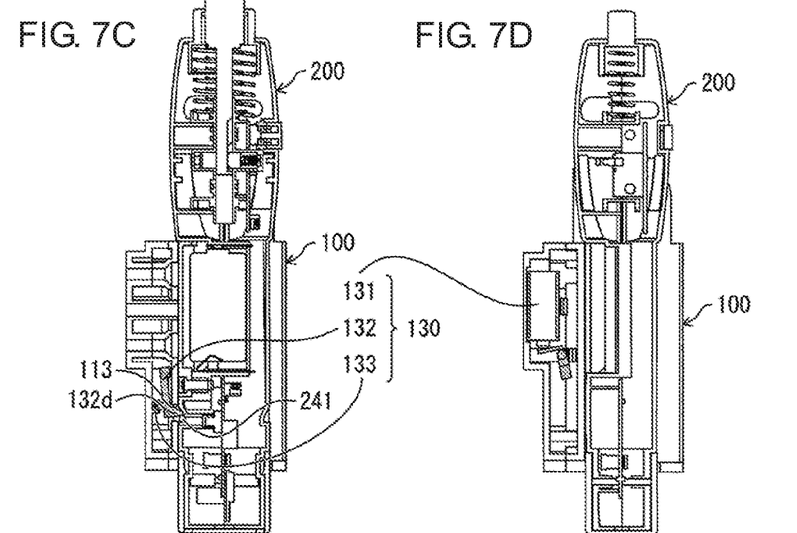

When powered on, the solenoid 131 attracts the plunger with a magnetic force to cause the movable plate 132 to pivot against the urging force (refer to FIGS. 7A and 7B). As the movable plate 132 moves with the solenoid 131 that is powered on, the hook 132d retracts from the hole 113 and is disengaged from the second engagement hole 242 in the operation device 200. This unlocks the operation device 200.

When powered off, the solenoid 131 losing the magnetic force stops attracting the plunger. The coil spring 133 causes the movable plate 132 to pivot in the same direction as the urging force (refer to FIGS. 7C and 7D). As the movable plate 132 moves with the solenoid 131 that is powered off, the hook 132d protrudes through the hole 113 and is engaged with the second engagement hole 242 in the operation device 200. This locks the operation device 200.

As described above, the holder 100 according to the present embodiment includes the lock mechanism 130, which switches between the lock mode in which the operation device 200 is unremovable and the unlock mode in which the operation device 200 is removable. The lock mechanism 130 enters the lock mode when the X-ray imaging device 1 is not in operation, and enters the unlock mode when the X-ray imaging device 1 is in operation.

The operation device 200 is locked when the imaging device is not in operation, and is unlocked when the imaging device is in operation. This structure can lock the operation device 200 being held in the holder when the X-ray imaging device 1 is powered off. The operation device 200 can be stored together with the X-ray imaging device 1, and is prevented from being brought away when the user stops keeping his or her eyes on the operation device 200 while the operation device 200 is not in use or is being carried around. This structure easily prevents the operation device 200 from being brought away.

When the operation device 200 is held in the holder in the lock mode, the hook 132d in the movable member 132 has its sloping surface in contact with the operation device 200 to press the hook 132d against its protruding movement. When the hook 132d faces the second engagement hole 242, the hook 132d, which has been pressed against its movement, is released to protrude and then is engaged with the second engagement hole 242.

The lock mechanism 130 in the holder 100 may be powered off after the X-ray imaging device 1 is powered off. More specifically, when the X-ray imaging device 1 is powered off, the lock mechanism 130 remains in the unlock mode while being powered, and then later enters the lock mode when it is powered off. In this structure, the solenoid 131 may be replaced by a motor.

In the present embodiment, the solenoid 131 losing the magnetic force permits the movable plate 132 to pivot in the urging direction. The hook 132d is then engaged with the operation device 200. When powered on, the solenoid 131 producing a magnetic force permits the movable plate 132 to pivot against the urging direction. The hook 132d is then disengaged from the operation device 200. However, the embodiment is not limited to this structure. The hook 132d may include a magnet, and the operation device 200 may include an iron core. In this structure, when the device is powered off, the magnet producing a magnetic force attracts the iron core. The hook 132d is then engaged with the second engagement hole 242. The lock mechanism enters the lock mode. When the device is powered on, the solenoid 131 producing a magnetic force causes the hook 132d to separate away from the iron core. The hook 132d is then disengaged from the second engagement hole 242. The lock mechanism then enters the unlock mode.

The operation device 200 may be housed in a case provided in the X-ray imaging device 1. The case may serve as the bringing-away preventive unit, and have a closure member that is open and closed to prevent the operation device 200 from being brought away.

In the present embodiment, although the operation device 200 is housed and locked with its front surface (including the optional switch 220 and the first engagement hole 241) exposed in front, and its back surface located at the back, the operation device 200 may be housed and locked with its back surface (including the second engagement hole 242) exposed in the front of the holder body 110, and its front surface (including the optional switch 220 and the first engagement hole 241) at the back of the holder body 110.

SUMMARY

As described above, a holding mechanism according to one aspect of the present invention is included in a main unit for holding an operation device in a removable manner. The operation device is used to operate the main unit wirelessly. The holding mechanism includes a bringing-away preventive unit that sets the operation device unremovable when the main unit is not in operation, and sets the operation device removable when the main unit is in operation.

The operation device with this structure is set unremovable when the main unit is not in operation, and is set removable when the main unit is in operation. This allows the operation device to be unremovable when the main unit is not in use, and to be removable when the main unit is in use. The operation device can thus be stored together with the main unit not in use, and is prevented from being brought away when the user stops keeping his or her eyes on the operation device while the operation device is being carried around. The holding mechanism with this structure for the operation device easily prevents the operation device from being brought away.

The bringing-away preventive unit included in the holding mechanism according to one aspect of the present invention includes a lock mechanism that switches between a lock mode in which the operation device is unremovable and an unlock mode in which the operation device is removable. The lock mechanism is switched to the lock mode when the main unit is not in operation, and to the unlock mode when the main unit is in operation.

In the above structure, the lock mechanism is switched to the lock mode when the main unit is not in operation, and to the unlock mode when the main unit is in operation. This locks the operation device when the main unit is not in use and unlocks the operation device when the main unit is in use. The operation device can thus be stored together with the main unit not in use, and is prevented from being brought away when the user stops keeping his or her eyes on the operation device while the operation device is being carried around.

The lock mechanism included in the holding mechanism according to one aspect of the present invention is powered off to enter the lock mode when the main unit is not in operation, and is powered on to enter the unlock mode when the main unit is in operation.

I the above structure, the lock mechanism enters the lock mode when it is powered off and enters the unlock mode when it is powered on.

The holding mechanism according to one aspect of the present invention further includes a contact member that comes in contact with at least a part of an outer surface of the operation device to hold the operation device. The lock mechanism includes a movable member including a hook that protrudes through a hole in the contact member, a drive that drives the movable member, and an elastic member that urges the movable member in a direction in which the hook protrudes through the hole in the contact member. The drive is not driven when the main unit is not in operation to cause the movable member to move in the urging direction and the hook to be engaged with the operation device, entering the lock mode. The drive is driven when the main unit is in operation to cause the movable member to move against the urging direction and the hook to be disengaged from the operation device, entering the unlock mode.

The lock mechanism included in the holding mechanism according to one aspect of the present invention includes a solenoid and an elastic member. When the main unit is not in operation, the solenoid is powered off to allow the elastic member to exert a force for entering the lock mode. When the main unit is in operation, the solenoid is powered on to exert a force for entering the unlock mode.

The operation device to be held in the holding mechanism according to one aspect of the present invention has a peripheral surface with an engagement hole that allows engagement with the hook. When the holding mechanism in the lock mode receives the operation device, the hook comes in contact with the operation device and is pressed against protruding, and the hook is released when the hook faces the engagement hole, and protrudes and is engaged with the engagement hole.

The lock mechanism included in the holding mechanism according to one aspect of the present invention sets the operation device unremovable when the holding mechanism receives the operation device after the holding mechanism without holding the operation device enters the lock mode.

The above structure locks the operation device when the holding mechanism in the lock mode receives the operation device.

An X-ray imaging unit according to one aspect of the present invention includes the holding mechanism, and an X-ray imaging device that detects X-rays and generates an X-ray image. The X-ray imaging device is the main unit.

The above structure provides the X-ray imaging unit that easily prevents an operation device from being brought away.

REFERENCE SIGNS LIST

1 X-ray imaging device (main unit)
100 holder (holding mechanism)
110 holder body (contact member)
130 lock mechanism (bringing-away preventive unit)
131 solenoid (drive)
132 movable plate (movable member)
132d hook
133 coil spring (elastic member)
200 operation device
241 first engagement hole
242 second engagement hole
300 X-ray imaging unit

The invention claimed is:
1. A holding mechanism included in a main unit for holding an operation device in a removable manner, the operation device being used to operate the main unit wirelessly, the holding mechanism comprising:
 a lock mechanism configured to:
  switch between a lock mode in which the operation device is unremovable and an unlock mode in which the operation device is removable, such that the lock mechanism is switched to the lock mode in response to the main unit not being in operation, and to the unlock mode in response to the main unit being in operation; and a contact member configured to come in contact with at least a part of an outer surface of the operation device to hold the operation device, wherein:

the lock mechanism comprises a movable member comprising a hook configured to protrude through a hole in the contact member, a drive configured to drive the movable member, and an elastic member configured to urge the movable member in a direction in which the hook protrudes through the hole in the contact member;

in response to the main unit not being in operation, the drive does not drive the movable member, thus causing the operation device to enter the lock mode by: the movable member to moving in the direction urged by the elastic member; the hook to protruding through the hole; and the hook to engaging with the operation device;

in response to the main unit being in operation, the drive drives the movable member, thus causing the operation device to enter the unlock mode by: the movable member moving in a direction opposite to the direction urged by the elastic member; and the hook being disengaged from the operation device; and the lock mechanism is further configured to set the operation device unremovable in response to the holding mechanism receiving the operation device after the holding mechanism, without holding the operation device, enters the lock mode.

2. The holding mechanism according to claim 1, wherein the lock mechanism is powered off to enter the lock mode in response to the main unit being not in operation, and is powered on to enter the unlock mode in response to the main unit being in operation.

3. A holding mechanism included in a main unit for holding an operation device in a removable manner, the operation device being used to operate the main unit wirelessly, the holding mechanism comprising:

a lock mechanism configured to: switch between a lock mode in which the operation device is unremovable and an unlock mode in which the operation device is removable, such that the lock mechanism is switched to the lock mode in response to the main unit not being in operation, and to the unlock mode in response to the main unit being in operation, wherein:

the lock mechanism comprises a solenoid configured to drive the movable member, and an elastic member;

in response to the main unit not being in operation, the solenoid is powered off so as to not drive the movable member, thus causing the operation device to enter the lock mode by: the movable member moving in a direction urged by the elastic member; and the hook engaging with the operation device;

in response to the main unit being in operation, the solenoid is powered on so as to drive the movable member, thus causing the operation device to enter the unlock mode by: the movable member moving in a direction opposite to the direction urged by the elastic member; and the hook being disengaged from the operation device; and the lock mechanism is further configured to set the operation device unremovable in response to the holding mechanism receiving the operation device after the holding mechanism, without holding the operation device, enters the lock mode.

4. The holding mechanism according to claim 1, wherein:

the operation device comprises a peripheral surface with an engagement hole that allows engagement with the hook; and in response to the holding mechanism in the lock mode receiving the operation device, the hook comes in contact with and presses against the operation device, and the hook is released in response to the hook facing and engaging with the engagement hole.

5. An X-ray imaging unit, comprising:

the holding mechanism according to claim 1; and an X-ray imaging device configured to detect X-rays and generate an X-ray image, the X-ray imaging device being the main unit.

6. An X-ray imaging unit, comprising:

the holding mechanism according to claim 3; and an X-ray imaging device configured to detect X-rays and generate an X-ray image, the X-ray imaging device being the main unit.

* * * * *